(12) United States Patent
Muramatsu et al.

(10) Patent No.: US 8,226,628 B2
(45) Date of Patent: Jul. 24, 2012

(54) COMMUNICATING NEEDLE FOR CONNECTING TWO OR MORE CONTAINERS TO COMMUNICATE

(75) Inventors: Yasuhiro Muramatsu, Shizuoka (JP); Shouichi Kitagawa, Shizuoka (JP)

(73) Assignee: Ajinomoto Co., Inc., Tokyo (JP)

( * ) Notice: Subject to any disclaimer, the term of this patent is extended or adjusted under 35 U.S.C. 154(b) by 264 days.

(21) Appl. No.: 11/670,638

(22) Filed: Feb. 2, 2007

(65) Prior Publication Data
US 2007/0208320 A1    Sep. 6, 2007

Related U.S. Application Data

(63) Continuation of application No. PCT/JP2005/014320, filed on Aug. 4, 2005.

(30) Foreign Application Priority Data

Aug. 4, 2004 (JP) ................................ 2004-228268

(51) Int. Cl.
*A61B 19/00* (2006.01)

(52) U.S. Cl. ........ 604/413; 604/403; 604/411; 604/414; 604/415

(58) Field of Classification Search ............... 251/149.1; 222/153.01, 153.05, 153.06; 604/403, 411, 604/414, 415, 416, 905, 317
See application file for complete search history.

(56) References Cited

U.S. PATENT DOCUMENTS

| | | | | |
|---|---|---|---|---|
| 4,244,364 A | * | 1/1981 | Grushkin | 604/254 |
| 4,253,459 A | * | 3/1981 | Willis | 604/414 |
| 4,340,049 A | * | 7/1982 | Munsch | 604/29 |
| 4,410,321 A | | 10/1983 | Pearson et al. | |
| 4,589,879 A | | 5/1986 | Pearson | |
| 4,675,020 A | * | 6/1987 | McPhee | 604/411 |
| 4,863,454 A | * | 9/1989 | LaBove | 604/416 |
| 5,067,950 A | * | 11/1991 | Broadnax, Jr. | 604/317 |
| 5,195,988 A | * | 3/1993 | Haaga | 604/265 |
| 5,279,605 A | * | 1/1994 | Karrasch et al. | 604/403 |
| 5,304,163 A | * | 4/1994 | Bonnici et al. | 604/403 |
| 5,380,315 A | * | 1/1995 | Isono et al. | 604/416 |
| 5,470,327 A | * | 11/1995 | Helgren et al. | 604/411 |
| 5,580,351 A | * | 12/1996 | Helgren et al. | 604/411 |
| 5,662,642 A | * | 9/1997 | Isono et al. | 604/403 |

(Continued)

FOREIGN PATENT DOCUMENTS

CA    1117488    2/1982

(Continued)

OTHER PUBLICATIONS

U.S. Appl. No. 12/512,427, filed Jul. 30, 2009, Muramatsu.

(Continued)

*Primary Examiner* — Leslie Deak
*Assistant Examiner* — Adam Marcetich
(74) *Attorney, Agent, or Firm* — Oblon, Spivak, McClelland, Maier & Neustadt, L.L.P.

(57) ABSTRACT

An object is to provide a communicating needle of simple construction which is attached to a medical infusion bag to connect two or more containers in fluid communication with each other. The communicating needle for connecting two or more containers to communicate includes a tip having an outlet opening formed thereon and a seal member integrally formed with the communicating needle to seal the outlet opening. The seal member readily comes off the communicating needle when acted upon by an external force, causing the outlet opening to open. The communicating needle may be covered by a seal body.

11 Claims, 6 Drawing Sheets

U.S. PATENT DOCUMENTS

| | | | |
|---|---|---|---|
| 5,776,125 A | 7/1998 | Dudar et al. | |
| 6,068,011 A * | 5/2000 | Paradis | 137/1 |
| 6,113,583 A * | 9/2000 | Fowles et al. | 604/403 |
| 6,132,413 A * | 10/2000 | Mathias et al. | 604/403 |
| 6,572,592 B1 * | 6/2003 | Lopez | 604/256 |
| 6,629,962 B2 * | 10/2003 | Correa et al. | 604/272 |
| 8,002,751 B2 * | 8/2011 | Carr | 604/190 |
| 2002/0066686 A1 * | 6/2002 | Montenieri et al. | 206/365 |
| 2002/0151843 A1 * | 10/2002 | Correa et al. | 604/82 |
| 2007/0060903 A1 | 3/2007 | Miyajima et al. | |
| 2008/0033390 A1 | 2/2008 | Kitagawa et al. | |
| 2008/0097372 A1 | 4/2008 | Shimizu et al. | |

FOREIGN PATENT DOCUMENTS

| | | |
|---|---|---|
| FR | 2 788 431 | 7/2000 |
| JP | 61-501129 | 6/1986 |
| JP | 63-501269 | 5/1988 |
| JP | 1-94856 | 4/1989 |
| JP | 3-501456 | 4/1991 |
| JP | 5-52748 | 8/1993 |
| JP | 6-054889 | 3/1994 |
| JP | 11-512014 A | 10/1999 |
| JP | 11-512014 A5 | 10/1999 |
| JP | 2000-316951 | 11/2000 |
| JP | 2003-220116 | 8/2003 |
| WO | WO 85/03432 | 8/1985 |
| WO | WO 87/02239 | 4/1987 |
| WO | WO 90/03536 | 4/1990 |
| WO | WO 96/00053 | 1/1996 |
| WO | WO 97/09025 | 3/1997 |

OTHER PUBLICATIONS

U.S. Appl. No. 12/436,172, filed May 6, 2009, Muramatsu.
Office Action issued May 20, 2011 in Japan Application No. 2006-531553 (With English Translation).

* cited by examiner

COMMUNICATING NEEDLE FOR CONNECTING TWO OR MORE CONTAINERS TO COMMUNICATE

TECHNICAL FIELD

The present invention relates to a communicating needle for connecting two or more containers to communicate so that the contents of the two or more containers can be mixed with each other. The present invention further relates to a port that includes the communicating needle and is used in the production of medical bags for containing pharmaceutical preparations and solutions.

BACKGROUND ART

Conventionally, a connector or a syringe has been used to mix a hypertonic amino acid preparation with a total parenteral nutrition base solution. In preparing an injection using antibiotic powder sealed in a vial, distilled water for injection or physiological saline is withdrawn by a syringe and injected into the vial to dissolve the antibiotic.

Infusion fluids are in many cases administered to patients by intravenous drip infusion. Of the different solutions that make up the infusion fluids, amino acid solutions and glucose solutions react with each other when mixed and are therefore stored in different compartments that are defined by peelable separators within an infusion bag. Upon use, the infusion bag is pressed from the outside to force the separators to peel, allowing the solutions to mix.

Upon administration of an infusion fluid to a patient by intravenous drip infusion, small amounts of additional drugs need to be added to the base solution, such as amino acid solution and glucose solution, of the infusion fluid depending on the condition of the patient. Among such drugs are trace minerals, vitamins, analgesics, fat infusions, antibiotics, minerals and cardiac stimulants. In general, mixing of the small amount of the drugs with the base solution is performed in a clean booth in the hospital. During the mixing process, a communicating tube or a syringe is used to inject the drugs into an infusion bag containing the infusion fluid. Care must be taken to prevent contamination of the fluid with bacteria.

When small amount of drugs are mixed with an infusion fluid, it is often undesirable to leave the mixed infusion fluid prior to administration because many of the drugs readily decompose once mixed. For example, decomposition of vitamin $B_1$ is facilitated by sulfite, an oxidizing agent used to oxide amino acids in the total parenteral nutrition base solution. When mixed, these drugs react with each other to form contaminants or facilitate the decomposition of each other. Some drugs are preferably administered at intervals. Generally provided in a volume of about 1 L, infusion fluids are not suitable for intricate adjustment and can only be mixed with a limited number of additional drugs.

Mixing and dissolving the additional drugs in infusion fluids involves the use of connector tubes and syringes, which not only makes the process complicated, but also requires a number of additional operations including connecting connector tubes and syringes and piercing bags of different solutions with a needle. Thus, the chance is high that the infusion fluids are contaminated with bacteria during the mixing process. Furthermore, the drugs remaining in syringes and the like after these operations lead to a considerable loss.

In an effort to counteract these problems, different types of premix infusion bags have been developed. For example, Patent Document 1 describes a premix infusion bag, which includes: a flexible infusion bag, a bottle needle directly attached to at least one part of the bag, a passage formed through the bottle needle in communication with the interior of the bag, a seal arranged in the passage of the bottle needle so that it shuts off the communication between the bottle needle and the interior of the bag, and a breakable element arranged in the passage so that it can be broken to open the communication between the bottle needle and the interior of the bag. The seal is arranged inside the bag and the breakable element is arranged between the inner periphery of the bag and the seal.

Patent Document 2 discloses a medical infusion bag, which includes: a first chamber, a second chamber and a single sub-chamber that are each defined by flexible resin film and can each pack a pharmaceutical fluid; and easy-peel seals disposed between the first and the second chambers and between the second and the sub-chambers, respectively, the easy-peel seals peeling under different pressures. Upon use, the pharmaceutical solution in the first chamber or the second chamber is mixed with the pharmaceutical solution in the sub-chamber via a nozzle extending from the sub-chamber.

Patent Document 1: Japanese Patent Publication No. Hei 5-52748

Patent Document 2: Japanese Patent Laid-Open Publication No. 2000-316951

The medical infusion bags disclosed in these patent documents each have a configuration in which a flexible plastic bag has separate compartments for individual infusion fluids. Upon use, the compartments are connected in fluid communication with each other, for example, by applying external force to mix the infusion fluids. This feature inevitably limits the number of infusion fluids that can be packed in a single medical bag. As a result, the applicability of these infusion bags is significantly limited. Thus, there is a need for a simple communicating needle that can be used with a wide variety of medical infusion bags to connect two or more containers in fluid communication with each other. It is necessary that such a communicating needle does not have the problems of infusion fluids remaining in the containers or infusion fluids contaminated with debris resulting from the broken seals.

DISCLOSURE OF THE INVENTION

Problems to be Solved by the Invention

In view of the above-mentioned problems, it is an object of the present invention to provide a simple communicating needle that is attached to medical infusion bags and the like and serves to connect two or more containers in fluid communication with each other.

The conventional mixing needles (communicating needle) used with multiple infusion sets are double-ended metal needles that not only include numerous parts, but also produce metal medical waste that must be separately collected. The communicating needle provided by the present invention has eliminated these problems.

Means for Solving the Problems

In an effort to address these problems, the present inventors have devised a novel communicating needle for connecting two or more containers in fluid communication. The communicating needle has an outlet opening for pharmaceutical solution formed at the tip thereof and has a seal member for sealing the outlet opening formed integrally therewith. The seal member can readily be snapped off by applying an external force. This causes the outlet opening to open. Such a construction facilitates mixing of pharmaceutical solutions contained in two or more containers with a base solution. This finding has led to complete the invention.

Specifically, one essential aspect of the present invention includes:

(1) A communicating needle for connecting two or more containers in fluid communication, comprising: a tip having an outlet opening formed thereon; and a seal member integrally formed with the communicating needle to seal the outlet opening, wherein the seal member readily comes off the communicating needle when acted upon by an external force to open the outlet opening on the communicating needle.

More specifically, the present invention includes the following:

(2) The communicating needle according to the above-described (1), further comprising a seal body that covers the communicating needle.

(3) The communicating needle according to the above-described (2), wherein the seal member includes the seal body which covers at least the tip of the communicating needle that is integrally formed therewith, such that the seal member comes off the communicating needle and remains within the seal body as the communicating needle is moved within the seal body.

(4) The communicating needle according to the above-described (3), wherein the movement of the communicating needle within the seal body involves piercing the seal body.

(5) The communicating needle according to the above-described (3), wherein the movement of the communicating needle within the seal body is caused by the rotation of the seal body.

(6) The communicating needle according to the above-described (1), further comprising a seal body that has a longitudinal slit to engage the seal member and covers the communicating needle, wherein the seal member comes off the communicating needle as the seal body is rotated.

(7) The communicating needle according to any of the above-described (2) to (6), wherein the seal body for covering is formed of an elastic material.

(8) The communicating needle according to the above-described (7), wherein the elastic material is selected from the group consisting of rubber, foamed rubber, plastic and hard plastic.

(9) The communicating needle according to any of the above-described (1) to (8), formed of hard plastic.

Even more detailed aspect of the present invention include the following:

(10) The communicating needle according to any of the above-described (1) to (9), used as a needle attached to an opening of a medical container containing a pharmaceutical solution, for mixing the pharmaceutical solution.

(11) The communicating needle according to the above-described (10), wherein the medical container, to which the communicating needle is attached, is a plastic film mixing container designed to be connected in fluid communication with a flexible infusion bag for mixing the pharmaceutical solution.

(12) The communicating needle according to the above-described (10), wherein the medical container is a single chamber container or a multiple chamber container having two or more chambers.

Another aspect of the present invention includes the following:

(13) A port to be welded to a flexible bag, comprising the communicating needle according to the above-described (1) to (9).

(14) The port according to the above-described (13), formed to have either a round, diamond, or planar oval shape.

Advantage of the Invention

Unlike conventional double-ended metal needles that are used in infusion sets for mixing purposes, the communicating needle for connecting two or more containers in fluid communication provided in accordance with the present invention has an outlet opening, for mixing infusion fluids, formed on the communicating needle and a seal member that is formed integrally with the communicating needle to seal the outlet opening, such that when an external force is applied, the seal member readily comes off the communicating needle to connect two or more containers in fluid communication. The communicating needle of the present invention constructed in this manner consists of considerably fewer parts than conventional double-ended needles.

The communicating needle and the seal member to seal the outlet opening may together be covered by a seal body made of rubber or other materials so that the seal member will readily come off the communicating needle by an external force applied when the communicating needle is rotated within the seal body or the communicating needle is moved to penetrate the seal body. Once coming off the communicating needle, the seal member remains within the seal body. This arrangement is advantageous in that the pharmaceutical agents or solutions contained in two containers can be safely mixed without contamination with debris or foreign matters.

The arrangement in which the communicating needle is integrated with the seal body is advantageous in that the sealed space formed between the communicating needle and the sealed body, as well as the seal member, can be completely sterilized by electron beam or gamma-ray radiation and, thus, a high level of hygiene can be maintained in a simple fashion during the mixing operation.

Unlike double-ended needles, which are made of metals, the communicating needle of the present invention is formed of a plastic having a proper hardness and can therefore be safely disposed of. Moreover, the material to make the communicating needle can be properly selected to prevent vitamins and other components in the container from being absorbed.

The port equipped with the communicating needle of the present invention for attachment to a flexible bag can be welded to a flexible bag of any shape and thus has high applicability.

BEST MODE FOR CARRYING OUT THE INVENTION

The communicating needle provided by the present invention for connecting two or more containers in fluid communication is preferably formed of a hard plastic. Examples of the hard plastic include acrylonitrile-styrene-butadiene (ABS) copolymers, polypropylene (PP) resins, polyethylene (PE) resins, hard polyvinyl chloride (PVC) resins, polycarbonate (PC) resins and cyclo-olefin polymers (COP). Of these, PVC and PC are particularly preferred because of their formability and fracture property.

The medical container, or the bag, to which the communicating needle of the present invention is attached is made of plastic film. Such plastic film may be provided in the form of a tube or a sheet and may itself a single-layered or multi-layered film. The film may in fact be made of any material that can be welded to itself by heating or pressing. Examples of such materials include polyolefin, such as low-density polyethylene, high-density polyethylene, polypropylene and cyclo-olefin polymers; and thermoplastic resins, such as polystyrene, acrylonitrile-styrene (AS) copolymer resins, acrylonitrile-butadiene-styrene (ABS) copolymer resins, acryl resins, vinyl chloride resins and nylon. Of these, are preferably used to make single-layered medical bags.

To attach to the bag, the communicating needle of the present invention is constructed as a port that can be welded to the bag with a communicating needle. The port may be a round, diamond or planar oval port, or it may be a tube of any shape. The port or the tube is also formed of a hard plastic and is welded and attached to a desired medical bag to provide a desired function.

The seal body to cover the communicating needle may be made of any film, tube or molded article, and the present invention is not limited thereto. While the material of the seal body may also be any suitable material, elastic materials are preferred, including rubbers, such as butyl rubber, isoprene rubber and natural rubber, and elastomers, such as styrene-based elastomers, olefin-based elastomers, polyester-based elastomers and nylon-based elastomers. Thermoplastic resins may also be used, including low-density polyethylene, high-density polyethylene, polypropylene and cyclo-olefin polymers. These materials may be used either individually or in combination of two or more.

The communicating needle, whether attached to the bag or not, may be integrated with the seal body by heat-welding or ultrasonic welding or by fitting engagement. The material to make these components may also be any material that can provide a desired function.

The communicating needle provided by the present invention may be of any thickness and length as long as the needle can serve to connect two or more containers in fluid communication with each other for mixing the contents of the containers. The tip of the needle may not be sharp, particularly considering the fact that blunt needles are increasingly used in clinical practice to avoid accidents by sharp needles and parts to be pierced by the communicating needle (i.e., rubber plug) generally include a slit to guide the needle.

The communicating needle provided by the present invention may be manufactured by any suitable technique. While it is typically manufactured by injection molding or machining, injection molding is preferred because the technique is suitable for mass production and industrialization. The seal member may be formed integrally with the communicating needle, or it may be formed separately from the needle and thereafter secured to the needle by machining or fitting engagement. Preferably, the seal member is formed integrally with the communicating needle.

The communicating needle of the present invention may be welded to the infusion bag via a port bearing the communicating needle. Thus, the present invention also relates to such a port having the communicating needle.

The port to be welded to the bag may be a round, diamond or planar oval port, or it may be a tube of any shape. The port may be formed integrally with the communicating needle, or it may be formed separately from the needle and thereafter secured to the needle by machining or fitting engagement. Preferably, the port is formed integrally with the communicating needle.

The bag to which the communicating needle of the present invention is attached may be manufactured by any suitable technique. For example, such a bag may be made by first forming a film by T-die molding or inflation molding, followed by blow molding to weld the film into a container shape.

Similarly, the seal body to cover the communicating needle may be manufactured by any suitable technique. For example, the seal body may be generally manufactured by T-die molding and inflation molding to make films, extrusion to make tubes, injection molding and blow molding to make molded articles, two-step molding with the communicating needle and insert molding. The seal body may be secured to the communicating needle or the bag bearing the communicating needle by heat-welding or ultrasonic welding, or by fitting engagement.

Example 1

The present invention will now be described in detail with reference to examples and accompanying drawings.

With reference to FIG. 1, an exemplary communicating needle 1 of the present invention is schematically illustrated. The communicating needle 1 includes a point 10 that is configured to have a tapered face with an acute angle enough to penetrate/pierce a rubber plug of a separate container. A communicating groove 11 is formed within the communicating needle.

In this example, the communicating needle 1 is a generally round needle and consists of the following three portions with increasing thicknesses from the point 10 having an acute angled needle shape: a tip portion 12, a mid portion 16, and a base portion 17. Although the needle in this example has such a construction, the communicating needle of the present invention may be constructed in any fashion as long as the intended function of the communicating needle is achieved.

The communicating needle 1 of the present invention includes outlet openings 13 formed in the tip portion 12 thereof. The outlet openings 13 each communicate with the communicating groove 11. Seal members 14, 15 are formed integrally with the communicating needle in such a manner that the seal members seal the respective outlet openings 13. The seal members 14, 15 are constructed to readily come off the communicating needle when acted upon by an external force. In this figure, the seal members 14, 15 are wing-shaped members integrally formed with the communicating needle. While the seal members in this example are wing-shaped, other shapes are also contemplated, including rod-shape and plate-shape. The seal members may be provided in any shape that can provide the desired function.

In the example shown in the figure, the two outlet openings 13 are symmetrically formed in the tip portion 12 of the communicating needle 1 with respect to the central axis of the communicating needle. While two outlet openings 13 are provided in this example, a single opening or two or more openings may also be possible.

The communicating needle 1 having the above-described construction is attached to an infusion bag (not shown) or the like bag for mixing purposes. Upon use, an external force is applied to remove the seal members 14, 15 from the tip portion 12 of the communicating needle 1 and to thus cause the outlet openings 13 to open. The communicating needle 1 then is pierced and inserted through a rubber plug of another container to connect the two containers in fluid communication with each other, allowing the mixing of the contents of the two containers.

As described above, the seal members (wing-shaped seal members in the figure) for sealing the outlet openings 13 are integrally formed with the communicating needle. In this regard, the communicating needle 1 and the seal members 14, 15 may be formed as an integral unit, or they may be formed separately and thereafter joined together by heating or ultrasonic treatment.

FIG. 2 shows a side explanatory view of the communicating needle 1 of Example 1 shown in FIG. 1. The same reference numerals denote the same elements as in FIG. 1: The communicating needle 1 includes the outlet openings 13 formed in the tip portion 12 thereof with each opening in communication with the communicating groove 11.

With reference to FIG. 3, another example of the communicating needle of the present invention is shown. Like reference numerals denote like elements in FIG. 1. In this example, the communicating needle 1 and the seal members 14, 15 integrally formed with the communicating needle 1 to seal the outlet openings 13 are covered by a seal body 20, or a cap, in its entirety, from the point 10 to the base portion 17. A gap 21 is formed between the seal body 20 and the communicating needle 1 about the mid portion 16 of the communicating needle 1. The gap 21 facilitates the smooth movement of the communicating needle 1 within the seal body 20 (cap).

The communicating needle 1 having the above-described construction is attached to an infusion bag (not shown) or the like bag for mixing purposes. Upon use, the communicating needle 1 is rotated within the seal body 20 covering the communicating needle 1 or the communicating needle 1 is moved to penetrate the seal body 20, thereby applying an external force to the seal members 14, 15, for sealing the outlet opening 13, integrally secured to the seal body 20. This causes the seal members 14, 15 to come off the communicating needle 1 and the outlet openings 13 to open. The communicating needle 1 is then pierced or inserted through a rubber plug of another container to connect the two containers in fluid communication with each other, allowing the mixing of the contents of the two containers.

The seal members 14, 15 that have come off the communicating needle 1 will remain within the seal body, saving time and effort in collecting debris.

While in this example, the seal body 20, or cap, covers the entire length of the communicating needle 1 from the point 10 down to the base portion 17 of the communicating needle 1, the seal body 20 can provide the desired function as long as it covers the communicating needle 1 from the point 10 to the seal members 14, 15 sealing the outlet openings 13.

While in this example, the seal body 20 to cover the communicating needle 1 is formed of an elastic material such as rubber or foamed rubber, it may be made of various other materials as described previously.

In this example, the seal members 14, 15 sealing the outlet openings 13 are removed by the rotary movement or piercing movement of the communicating needle 1 within the seal body 20 (cap). Upon use, the communicating needle 1 covered entirely by the sack-like seal body 20, together with the seal members 14, 15 integrally formed with the communicating needle 1 to seal the outlet openings 13, is pierced and inserted through a mixing port (i.e., rubber plug) of an infusion bag. Accordingly, the seal body 20 is urged against the mixing port of the bag, and an external force acts on the seal members 14, 15 integrally formed with the communicating needle to seal the outlet openings 13, causing the seal members 14, 15 to come off the communicating needle 1 and the outlet openings 13 to open. Once the needle penetrates the mixing port (i.e., rubber plug) of the infusion bag, the mixing is effected in this status.

In one modification of the communicating needle 1 of the present invention, a covering member 30 having longitudinal slits covers the communicating needle 1. The longitudinal slits engage wing-shaped seal members 14, 15. As the covering 30 is rotated about the needle, the seal members come off the needle. Unlike the seal body 20 (cap) described in Example 3, the covering member 30 does not need to extend along the entire length of the communicating needle 1. The covering member 30, having the longitudinal slits to engage the seal members 14, 15, can be likewise rotated about the communicating needle 1 to remove the seal members 14, 15 from the communicating needle 1. The seal members 14, 15 that have come off the communicating needle 1 will remain within the covering member, saving time and effort in collecting debris.

This modification is illustrated as Example 3 in FIG. 4, in which like reference numerals denote like elements in FIG. 1. In the communicating needle 1 shown in FIG. 4, the covering member 30 having the longitudinal slits to engage the seal members 14, 15 is the same as in Example 2, except that it includes longitudinal slits (not shown) to engage the seal members 14, 15 and it does not cover the entire length of the communicating needle including the point of the needle. The covering member 30 does not cover the entire length of the communicating needle 1: it covers the needle down to the mid portion.

Another modification is illustrated as Example 4 in FIG. 5, in which like reference numerals denote like elements in FIG. 1. The communicating needle 1 in Example 4 includes a seal member 14 to seal an outlet opening 13. When the communicating needle 1 is made in communication with a flexible infusion bag, the communicating needle 1 is moved to be pierced through a part to be pierced (i.e., rubber plug) and the piercing movement of the communicating needle 1 exerts an external force on a engaging member 18 formed on the seal member 14 with the use of the part to be pierced. This causes the seal member 14 to come off the needle and the outlet opening 13 to open.

When the seal member 14 comes off the communicating needle 1, the seal member may be guided by a guide member that is integrally formed with the communicating needle. An engaging member 15 may also be formed integrally with the communicating needle 1.

Still another modification is illustrated as Example 5 in FIG. 6, in which like reference numerals denote like elements in FIG. 1. As in Example 4, an outlet opening 13 in Example 5 is sealed with a seal member 14. As the communicating needle 1 is pierced through a part to be pierced (i.e., rubber plug), the piercing movement of the needle exerts an external force on the seal member 14 with the use of the part to be pierced, causing the seal member to snap off. The seal member 14 in this example, however, is connected to the communicating needle 1 via an anchor member 19, which prevents the seal member 14 from coming off the needle as debris.

The present invention also provides a port that has the above-described communicating needle and is welded to a flexible bag. The port with a communicating needle may be any port commonly used with medical bags, including round ports, diamond ports or planar oval ports.

With reference to FIG. 7, an exemplary diamond port is shown having the communicating needle according to Example 2 of the present invention.

Specifically, the port 100 (diamond port in the figure) provided by the present invention includes a communicating needle 1 of the invention and a welded part 35 welded to the base of the communicating needle 1. The port 100 is welded to a medical bag via the welded part 35.

In the production of medical bags, the port is integrally welded to a bag.

For ease of understanding, the port 100 of FIG. 7 is shown in side explanatory view in FIG. 8, in which like reference numerals denote like elements.

FIG. 9 illustrates a modification of the seal member 20, or the cap, for covering the entire length of the communicating needle 1 from the point 10 to the base portion 17. The cap 20 has a bellow-like construction and is used with a one pack-type medical bag 40 that has a port welded to it. The cap 20 is formed of a plastic material and has a top plate 25 that is thin enough to be readily pierced by the communicating needle.

INDUSTRIAL APPLICABILITY

As set forth, the communicating needle provided in accordance with the present invention for connecting two or more containers in fluid communication with each other includes at its tip an outlet opening for a pharmaceutical solution and has a seal member for sealing the outlet opening formed integrally with the communicating needle. The seal member readily comes off the communicating needle when acted upon by an external force, causing the outlet opening to open. Having such a construction, the communicating needle of the present invention facilitates mixing of pharmaceutical solutions contained in two or more containers with, for example, a base solution.

The communicating needle may also include a seal body that covers the needle and the seal member sealing the outlet opening. By applying an external force due to the rotation of the communicating needle within the seal body or the movement of the communicating needle, together with the seal body, so that the communicating needle pierces or penetrates the mixing port (i.e., rubber plug) of a mixing container, the seal member sealing the outlet opening readily comes off the communicating needle. The seal member that has come off the needle remains within the rubber seal body. In this manner, pharmaceutical agents or solutions contained in two containers can be safely mixed without contamination with debris or foreign matters.

REFERENCE NUMERALS

Figure 1:
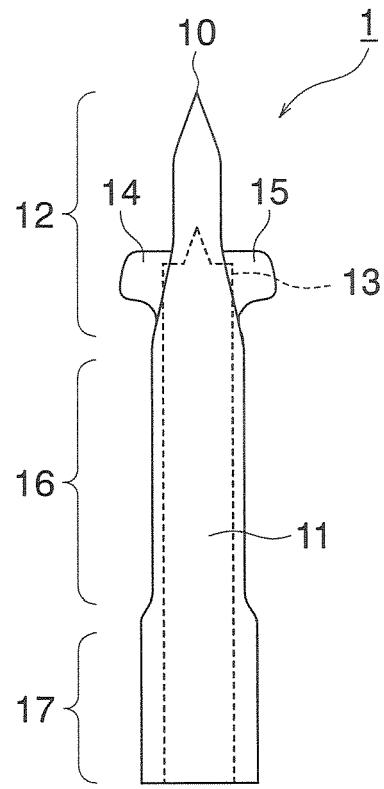
FIG. 1 is a schematic explanatory view of Example 1 of a communicating needle of the present invention.
Figure 2:
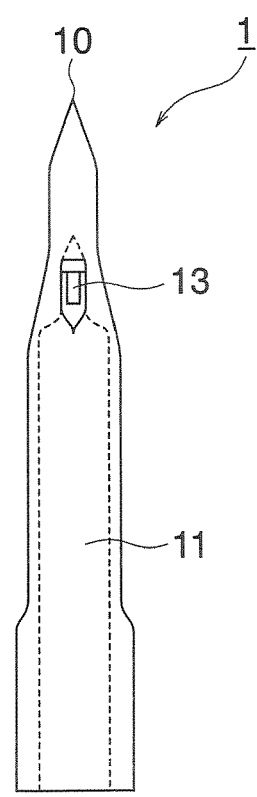
FIG. 2 is a side explanatory view of the communicating needle of Example 1 of the present invention.
Figure 3:
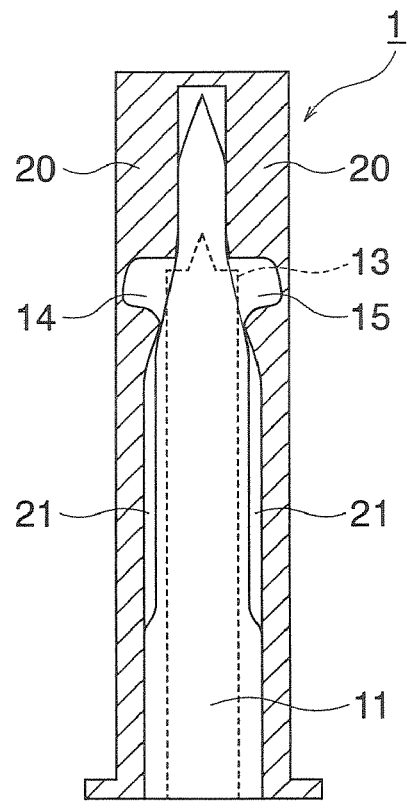
FIG. 3 is a schematic explanatory view of Example 2 of a communicating needle of the present invention.
Figure 4:
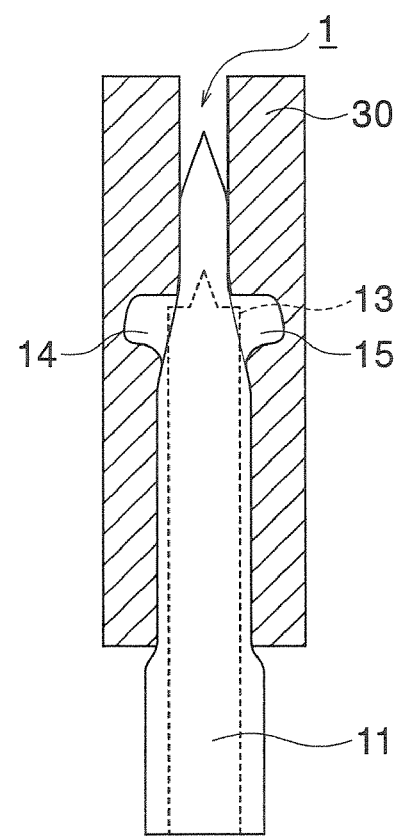
FIG. 4 is a schematic explanatory view of Example 3 of a communicating needle of the present invention.
Figure 5:
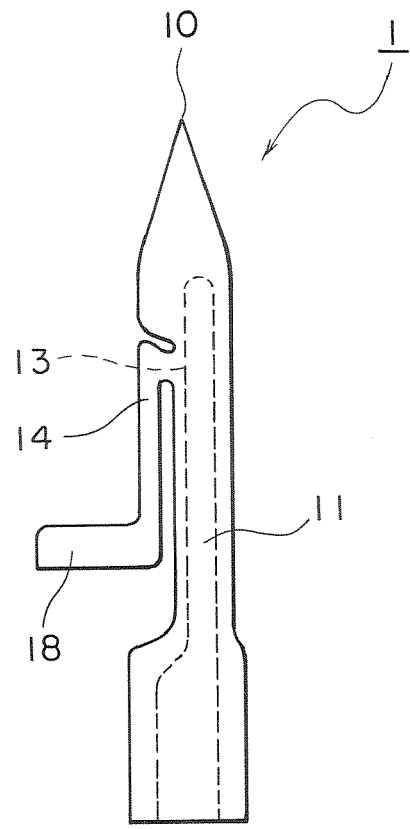
FIG. 5 is a schematic explanatory view of Example 4 of a communicating needle of the present invention.
Figure 6:
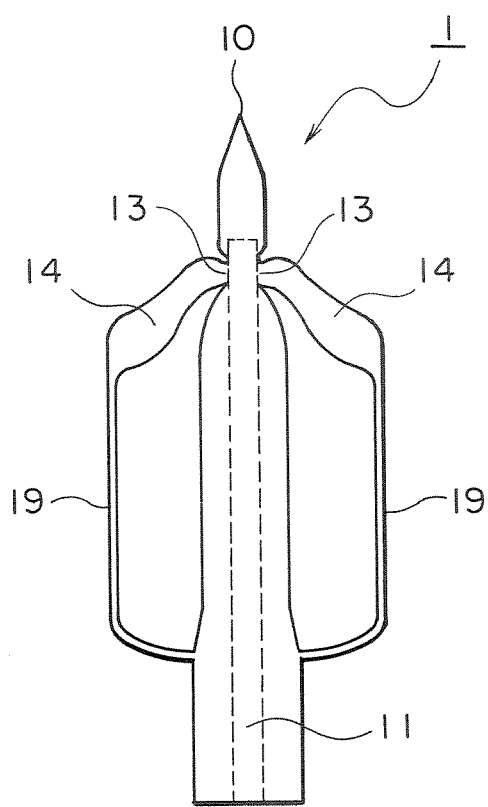
FIG. 6 is a schematic explanatory view of Example 5 of a communicating needle of the present invention.
Figure 7:
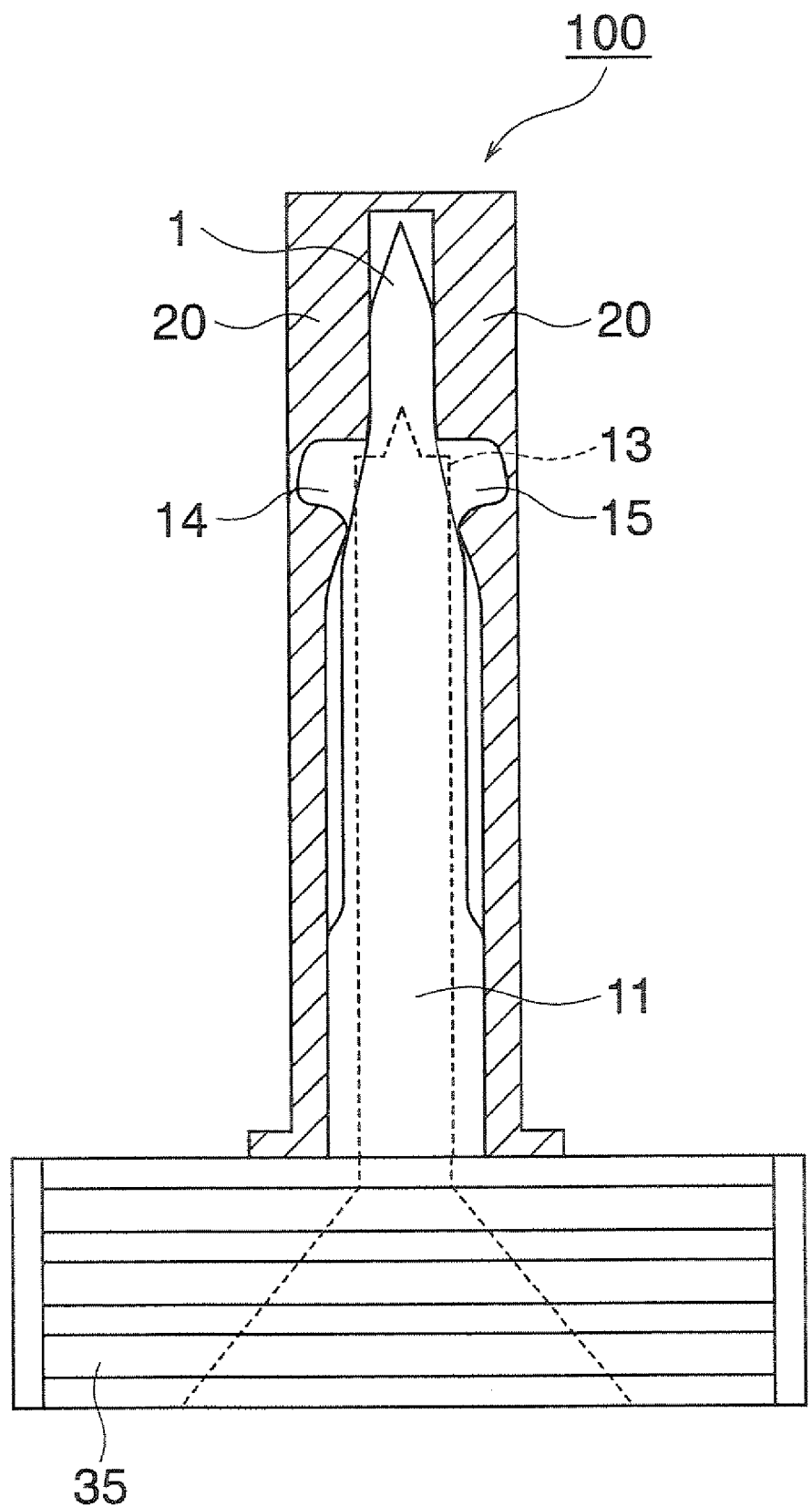
FIG. 7 is an explanatory view of a diamond port having the communicating needle of Example 2 of the present invention.
Figure 8:
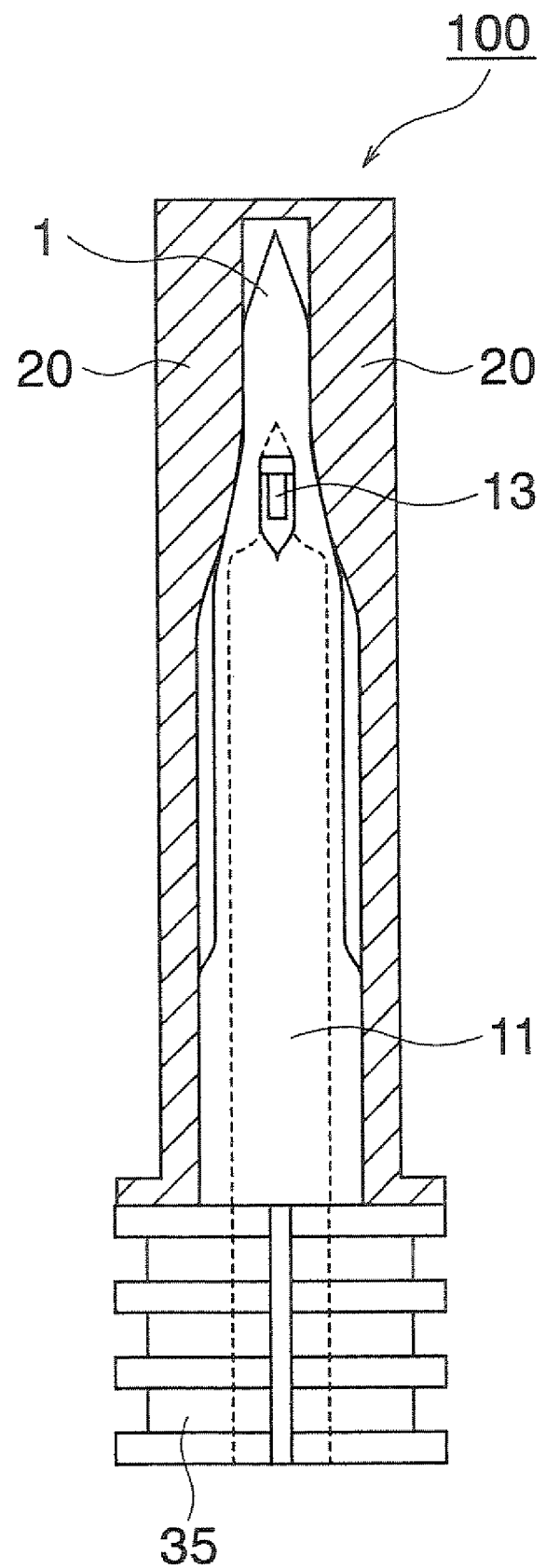
FIG. 8 is a side explanatory view of the diamond port having the communicating needle of the present invention.
Figure 9:
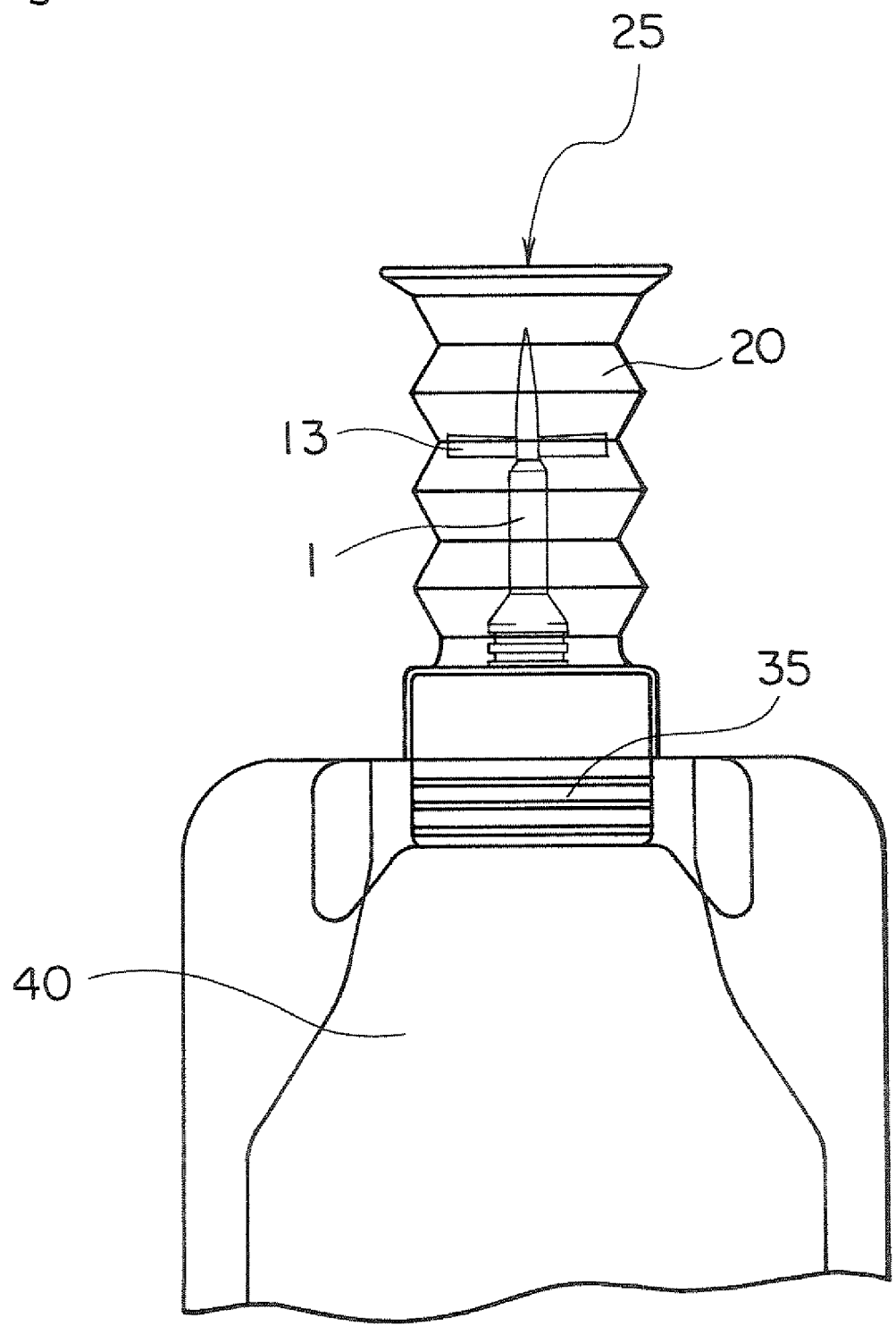
FIG. 9 is a partially cut explanatory view of a one pack-type medical bag having a port of the present invention and a bellow-shaped cup to serve as a cap to seal the communicating needle.

1. Communicating needle
10. Point
11. Communicating groove
12. Tip portion
13. Outlet opening
14. Seal member
15. Seal member
18. Engaging member
19. Anchor member
20. Seal body (Cap)
21. Gap
30. Covering member
35. Welded part
40. Medical bag
100. Port

The invention claimed is:

1. A communicating needle for connecting two or more containers in fluid communication, comprising:
    a piercing tip having an outlet opening formed thereon; and
    a seal member integrally formed with the communicating needle to seal the outlet opening, and
    a seal body that covers the communicating needle, wherein the communicating needle is formed of a hard plastic,
    wherein the seal member is configured to come off the communicating needle when acted upon by an external force to open the outlet opening on the communicating needle, and
    wherein the seal body is configured to cover at least the piercing tip of the communicating needle with which the seal member is integrally formed, such that the seal member is configured to come off the communicating needle and remains within the seal body as the communicating needle is moved within the seal body
    wherein the communicating needle is configured to pierce the seal body and or the seal members come off the communicating needle when the seal body rotates around the axis of the communicating needle.

2. The communicating needle according to claim 1, further comprising a seal body that has a longitudinal slit to engage the seal member and covers the communicating needle, wherein the seal member comes off the communicating needle as the seal body is rotated.

3. The communicating needle according to claim 1, wherein the seal body for covering is formed of an elastic material.

4. The communicating needle according to claim 3, wherein the elastic material is selected from the group consisting of rubber, foamed rubber, plastic and hard plastic.

5. The communicating needle according to claim 1, used as a needle attached to an opening of a medical container containing a pharmaceutical solution, for mixing the pharmaceutical solution.

6. The communicating needle according to claim 5, wherein the medical container, to which the communicating needle is attached, is a plastic film mixing container designed to be connected in fluid communication with a flexible infusion bag for mixing the pharmaceutical solution.

7. The communicating needle according to claim 5, wherein the medical container is a single chamber container or a multiple chamber container having two or more chambers.

8. A port to be welded to a flexible bag, comprising the communicating needle according to claim 1.

9. The port according to claim 8, formed to have either a round, diamond, or planar oval shape.

10. A communicating needle for connecting two or more containers in fluid communication, comprising:
    a piercing tip having an outlet opening formed thereon; and
    a seal member integrally formed with the communicating needle to seal the outlet opening, and
    an engaging member formed on the seal member, wherein the communicating needle is formed of a hard plastic, and wherein the seal member readily comes off the communicating needle when acted upon by an external force applied to said engaging member to open the outlet opening on the communicating needle wherein the seal member is configured to come off the communicating needle when the communicating needle pierces a stopper.

11. A communicating needle for connecting two or more containers in fluid communication, comprising:

a piercing tip having an outlet opening formed thereon;

a seal member integrally formed with the communicating needle to seal the outlet opening, and is connected to the communicating needle via an anchor member, and an anchor member formed on the seal member so as to prevent the seal member from coming off the needle, wherein the communicating needle is formed of a hard plastic, and wherein the seal member readily comes off the communicating needle when acted upon by an external force applied to open the outlet opening on the communicating needle wherein the seal member is configured to come off the communicating needle when the communicating needle pierces a stopper.

* * * * *